United States Patent
Evans, III et al.

(10) Patent No.: US 6,442,418 B1
(45) Date of Patent: Aug. 27, 2002

(54) TOTAL SYSTEM FOR CONTRAST DELIVERY

(75) Inventors: Russell Morrison Evans, III, Natrona Heights; Arthur E. Uber, III, Pittsburgh, both of PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 09/266,727

(22) Filed: Mar. 12, 1999

Related U.S. Application Data (62) Division of application No. 08/919,742, filed on Aug. 28, 1997, now Pat. No. 5,885,216, which is a division of application No. 08/534,081, filed on Sep. 22, 1995, now Pat. No. 5,806,519, which is a continuation of application No. 08/144,462, filed on Oct. 28, 1993, now abandoned.

(51) Int. Cl.$^7$ .................................................. A61M 5/00
(52) U.S. Cl. .................. 600/431; 600/432; 128/DIG. 12
(58) Field of Search ............................... 600/431, 432; 128/DIG. 1, DIG. 12, DIG. 13; 604/65–67, 82, 131, 151, 246, 247

(56) References Cited

U.S. PATENT DOCUMENTS

| | | |
|---|---|---|
| 3,349,713 A | 10/1967 | Fassbender |
| 3,523,523 A | 8/1970 | Reich |
| 3,701,345 A | 10/1972 | Heilman et al. |
| 3,755,655 A | 8/1973 | Sewecal |
| 3,793,600 A | 2/1974 | Groubard |
| 3,812,843 A | 5/1974 | Worstten et al. |
| 3,895,220 A | 7/1975 | Nelson et al. |
| 3,898,983 A | 8/1975 | Elam |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,038,981 A | 8/1977 | LeFevre et al. |
| 4,151,845 A | 5/1979 | Clemens |
| 4,187,057 A | 2/1980 | Xanthopoulos |
| 4,199,000 A | 4/1980 | Edstrom |
| 4,207,871 A | 6/1980 | Jenkins |
| 4,223,675 A | 9/1980 | Willaims |
| 4,262,824 A | 4/1981 | Hrynewycz |
| 4,280,494 A | 7/1981 | Cosgrove et al. |
| 4,319,568 A | 3/1982 | Tregouing |
| 4,340,153 A | 7/1982 | Spivey |
| 4,392,849 A | 7/1983 | Petre et al. |
| 4,396,385 A | 8/1983 | Kelly et al. |
| 4,434,822 A | 3/1984 | Bellamy et al. |
| 4,447,230 A | 5/1984 | Gula et al. |

(List continued on next page.)

FOREIGN PATENT DOCUMENTS

| | | |
|---|---|---|
| DE | 3726452 | 2/1989 |
| DE | 4121568 | 10/1992 |
| EP | 0 343 501 | 5/1989 |
| EP | 0 337 924 | 10/1989 |
| EP | 0 600 488 | 6/1994 |
| EP | 0 650 739 | 5/1995 |
| FR | 2493708 | 5/1982 |
| FR | 2561949 | 10/1985 |
| GB | 2 207 749 | 2/1989 |
| GB | 2252656 | 8/1992 |
| WO | WO80/01754 | 9/1980 |
| WO | WO85/00292 | 1/1985 |
| WO | Wo94/15664 | 7/1994 |

*Primary Examiner*—Ruth S. Smith
(74) *Attorney, Agent, or Firm*—Paul T. Bowen; Gregory L. Bradley (57) ABSTRACT

A disposable unit for delivering fluid medium to one of a plurality of patients includes a sterile patient supply tube, and structure for receiving pressurized fluid medium into the patient supply tube. One or more devices is provided for precluding backflow of material from the patient to the fluid medium receiving structure, for preventing contamination of the fluid medium receiving structure and/or for preventing cross-contamination between patients.

53 Claims, 2 Drawing Sheets

U.S. PATENT DOCUMENTS

| | | | |
|---|---|---|---|
| 4,479,760 | A | 10/1984 | Bilstad et al. |
| 4,479,761 | A | 10/1984 | Bilstad et al. |
| 4,479,762 | A | 10/1984 | Bilstad et al. |
| 4,544,949 | A | 10/1985 | Kurihara |
| 4,551,133 | A | 11/1985 | Zegers De Beyl et al. |
| 4,559,036 | A | 12/1985 | Wunsch |
| 4,563,175 | A | 1/1986 | LaFond |
| 4,585,009 | A | 4/1986 | Barker et al. |
| 4,610,670 | A | 9/1986 | Spencer |
| 4,610,790 | A | 9/1986 | Reti et al. |
| 4,634,426 | A | 1/1987 | Kamen |
| 4,636,144 | A | 1/1987 | Abe et al. |
| 4,682,170 | A | 7/1987 | Kubata |
| 4,710,166 | A | 12/1987 | Thompson et al. |
| 4,750,643 | A | 6/1988 | Wertrich |
| 4,754,786 | A | 7/1988 | Roberts |
| 4,783,273 | A | 11/1988 | Knutsson et al. |
| 4,798,590 | A | 1/1989 | O'Leary et al. |
| 4,835,521 | A | 5/1989 | Andrejasich et al. |
| 4,840,620 | A | 6/1989 | Kobayashi et al. |
| 4,853,521 | A | 8/1989 | Claeys et al. |
| 4,854,324 | A | 8/1989 | Hirschman |
| 4,857,056 | A | 8/1989 | Talonn |
| 4,879,880 | A | 11/1989 | Harrison |
| 4,880,014 | A | 11/1989 | Zarowitz et al. |
| 4,887,208 | A | 12/1989 | Schneider et al. |
| 4,887,554 | A | 12/1989 | Whitsord |
| 4,925,444 | A | 5/1990 | Orkin et al. |
| 4,929,818 | A | 5/1990 | Bradbury et al. |
| 4,943,279 | A | 7/1990 | Samiotes et al. |
| 4,946,256 | A | 8/1990 | Kumble |
| 4,946,439 | A | 8/1990 | Eggers |
| 4,950,245 | A | 8/1990 | Brown et al. |
| 4,978,335 | A | 12/1990 | Arthur, III |
| 4,981,467 | A | 1/1991 | Bobo, Jr. et al. |
| 5,009,654 | A | 4/1991 | Minshall et al. |
| 5,059,173 | A | 10/1991 | Sacco |
| 5,078,683 | A | 1/1992 | Sancoff et al. |
| 5,088,981 | A | 2/1992 | Howson et al. |
| 5,100,380 | A | 3/1992 | Epstein et al. |
| 5,128,121 | A | 7/1992 | Berg et al. |
| 5,180,896 | A | 1/1993 | Gibby et al. |
| 5,199,604 | A | 4/1993 | Palmer |
| 5,207,642 | A | 5/1993 | Orkin et al. |
| 5,230,614 | A | 7/1993 | Zanger et al. |
| 5,267,174 | A | 11/1993 | Kaufman et al. |
| 5,273,537 | A | 12/1993 | Haskvitz et al. |
| 5,274,218 | A | | 12/1993 | Vata |
| 5,310,997 | A | | 5/1994 | Roach |
| 5,313,992 | A | | 5/1994 | Grabenkort |
| 5,317,506 | A | | 5/1994 | Coutre et al. |
| 5,328,463 | A | | 7/1994 | Barten et al. |
| 5,329,459 | A | | 7/1994 | Kaufman et al. |
| 5,339,799 | A | | 8/1994 | Kami et al. |
| 5,349,625 | A | | 9/1994 | Born et al. |
| 5,354,273 | A | | 10/1994 | Hagen |
| 5,361,761 | A | | 11/1994 | Van Lysel et al. |
| 5,362,948 | A | | 11/1994 | Mormoto |
| 5,368,562 | A | | 11/1994 | Blomquist et al. |
| 5,378,231 | A | | 1/1995 | Johnson et al. |
| 5,385,540 | A | | 1/1995 | Abbott et al. |
| 5,417,213 | A | | 5/1995 | Prince |
| 5,431,627 | A | | 7/1995 | Pastrone et al. |
| 5,445,621 | A | | 8/1995 | Poli et al. |
| 5,450,847 | A | | 9/1995 | Kampfe et al. |
| 5,458,128 | A | | 10/1995 | Polanyi et al. |
| 5,460,609 | A | | 10/1995 | O'Donnell |
| 5,464,391 | A | | 11/1995 | DeVale |
| 5,472,403 | A | * | 12/1995 | Cornacchia et al. ........ 600/432 |
| 5,474,683 | A | | 12/1995 | Bryant et al. |
| 5,485,831 | A | | 1/1996 | Holdsworth et al. |
| 5,489,265 | A | | 2/1996 | Montalvo et al. |
| 5,494,036 | A | | 2/1996 | Uber, III et al. |
| 5,496,273 | A | | 3/1996 | Pastrone et al. |
| 5,507,412 | A | | 4/1996 | Ebert et al. |
| 5,515,851 | A | | 5/1996 | Goldstein |
| 5,522,798 | A | | 6/1996 | Johnson et al. |
| 5,531,679 | A | | 7/1996 | Schulman et al. |
| 5,531,697 | A | | 7/1996 | Olsen et al. |
| 5,533,978 | A | | 7/1996 | Teirstein |
| 5,547,470 | A | | 8/1996 | Johnson et al. |
| 5,553,619 | A | | 9/1996 | Prince |
| 5,569,208 | A | | 10/1996 | Woelpper et al. |
| 5,573,515 | A | | 11/1996 | Wilson et al. |
| 5,579,767 | A | | 12/1996 | Prince |
| 5,590,654 | A | | 1/1997 | Prince |
| 5,616,124 | A | | 4/1997 | Hague et al. |
| 5,799,649 | A | * | 9/1998 | Prince ........................ 600/432 |
| 5,800,397 | A | | 9/1998 | Wilson et al. |
| 5,840,026 | A | * | 11/1998 | Uber, III et al. ............ 600/431 |
| 5,882,343 | A | | 3/1999 | Wilson et al. |
| 5,916,165 | A | | 6/1999 | Duchon et al. |
| 5,988,587 | A | | 11/1999 | Duchon et al. |
| 6,099,502 | A | | 8/2000 | Duchon et al. |

* cited by examiner

Fig. 1

TOTAL SYSTEM FOR CONTRAST DELIVERY

This is a division of application Ser. No. 08/919,742, filed Aug. 28, 1997, now U.S. Pat. No. 5,885,216, which is a division of application Ser. No. 08/534,081, filed Sep. 22, 1995, now U.S. Pat. No. 5,806,519, which is a continuation of application Ser. No. 08/144,462, filed Oct. 28, 1993, abandoned.

BACKGROUND OF THE INVENTION

Contrast media are used in many medical diagnostic and therapeutic imaging procedures. Diagnostically these include X-ray procedures for instance, angiography, venography and urography, CT scanning, magnetic-resonance imaging [MRI], and ultrasonic imaging. Contrast media is used during therapeutic procedures such as angioplastic and other interventional radiologic procedures. Because this contrast material is injected into the patient, it must be sterile and contain a minimum of pyrogens.

Presently, most contrast is provided in sterilized glass bottles, ranging in size from 20 ml to 200 ml. Plastic packages are also available. Non-ionic X-ray contrast media is expensive, on the order of $1/ml. Ionic contrast media costs about $0.10/ml. Non-ion contrast has fewer complications but because of the cost, it is not universally used. MRI contrast costs about $5/ml. All the containers are single use, which means that once a bottle is opened, it should be used for that patient or thrown away, although a multi-use 1,000 ml bottle has been recently approved by the FDA.

A hospital must purchase and stock many concentrations in multiple bottle sizes to provide the right amount of the right concentration for a specific procedure, while minimizing the wastage of contrast remaining in any opened bottles.

This multitude of sizes and concentrations increases costs throughout the contrast supplier chain. Manufacturers need to make many batches with various concentrations, and package each in many sized bottles. They must have inventories of each on hand to quickly meet the customerts request. Each concentration and size entails an added regulatory burden.

In the hospital, there are additional costs due to the work purchasing the various brands and sizes, storage space is required for stocking, cabinets are required in each procedure room, and time is required to make sure the right numbers of each bottle are kept in each room. Frustration, waste and/or less than optimal studies can occur if this complex logistics chain fails at any point.

To illustrate the problem, consider a manufacturer who makes 5 concentrations of contrast, packages them in bottles of 10, 25, 50, 75, 100, 150 and 200 ml. The manufacturer now has 35 different products to get approval for, schedule production for, maintain sufficient stock of, and finally, ship to his customers.

Presently, most hospitals utilize a standard protocol for a given set of indications. For instance, for a CT scan of the liver, the protocol may call for 130 ml of contrast injected at 3 ml/s. This protocol is used for a wide variety of patient weights and physical conditions. One goal of this standardization is to minimize errors. Another is to decrease the likelihood of having to repeat the procedure, with the problem of additional radiation and contrast dose to the patient.

However, there are costs associated with this method. Many patients may get more contrast than they need for an image to be diagnostic. Overdosing wastes contrast, but there is no way with the present contrast supply and delivery system to remedy this, without stocking many more sizes of bottles and working harder to fill syringes. Other patients may have studies that are less than optimum. They do not receive enough contrast. The contrast that isn't used doesn't cost anything, but there is a much greater chance of having to repeat the whole procedure, with a much greater cost than a few milliliters of contrast. Again, using many bottle sizes and a cumbersome filling procedure is the only solution presently available.

In angiography, there are not set protocols to the same extent as in CT, because patient size determines vessel size which in turn determines the volume and flow rate needed. This means that a fixed amount of contrast cannot be prepared ahead of time with any confidence that more won't be needed during the procedure or that a significant amount won't remain and be wasted at the end of the procedure. To avoid delays while working on the patient, the technician loads more than the average amount used, with the realization that some is likely to be wasted, and there still is a chance that a delay will occur when more has to be loaded.

Another problem this system addresses is the volume and cost of items which must be disposed of after each patient. To save contrast, several small glass bottles may be opened per patient. One or more plastic syringes, and various tubing arrangements are used. There is a cost to purchase and a cost to dispose of each of these items.

The problems arising from the use of a multiplicity of concentrations and container sizes was addressed in German DE 4121568A1. In this disclosure, there is provided a supply tank of contrast agent that could contain from about 0.1 to as much as 100 liters. The device also included a similar tank that contained a diluent so that the composition of the resulting mixture could be varied to form a variety of concentrations. The abstract in the German patent utilizes a bulk mechanical mixer with sequential flow and so it would not seem to provide for the production of continuously variable concentrations. Nor, and importantly, is there any description of means to prevent cross-contamination when the apparatus is used on a plurality of patients.

Machines for mixing IV solutions also do not connect directly to the patient. Generally, the controls require that the operator know which fluid is in which position and that he choose the mixing ratios. In U.S. Pat. No. 4,341,153, medication is diluted and delivered to a syringe. There are no means described for connection to a patient, there is no mixing means and only sequential flows are described.

U.S. Pat. No. 4,610,790 describes in great detail how to make sterile water for diluting medications. Making diluted fluids is mentioned in little detail. U.S. Pat. No. 4,783,273 describes the use of sterilizing filters to assure the sterility of bulk fluids. Concentration monitors are also described. A serious drawback is the use of chemical sterilants.

In none of the references mentioned above is a mechanism described which can be used to sequentially or simultaneously inject contrast into several patients while minimizing the chance of cross-contamination. Nor is there any mention of information integrity or information transfer so that the proper procedures are followed with the diluted medications.

OBJECTS OF THE INVENTION

It is a principal object of this invention to provide an improved apparatus for injecting a contrast medium sequentially into a plurality of patients while minimizing the chance of cross-contamination.

It is another object of this invention to provide a contrast medium apparatus in which the degree of concentration of the contrast medium can be continuously varied.

It is another object of this invention to provide an apparatus for producing contrast medium in which the medium can either be injected directly into the patient or can be loaded into containers and then injected by means of an injecting apparatus.

Other objects and advantages of this invention will be, in part, obvious and, in part, explained by reference to the accompanying specification and the drawings in which:

DESCRIPTION OF THE INVENTION

It is a goal of this invention to enable delivery of only the amount of contrast needed to a patient, with minimal contrast waste. A companion goal is to be able to deliver whatever volume of contrast is needed, when it is needed, without the arbitrary limitation of syringe or mixing chamber size. The bulk containers can hold more fluid than would be given to one patient, so its size is not a limit.

This is accomplished by changing the way contrast is packaged and delivered to the patient. Bulk contrast bottles would be manufactured and distributed to the hospital in only a few number of sizes. A given procedure room would only stock one size of bottle. The bulk contrast could only be available in a single high concentration, the highest used in current procedures, or it may be available in a limited number of different concentrations. Two bottle sizes times two concentrations is only four variations that a manufacturer would potentially have to deal with.

It is possible to eliminate the multiplicity of concentrations by providing bulk diluent and having a contrast delivery system be able to dilute the most concentrated contrast to any concentration which the doctor desires. The diluent may be sterile water if the contrast is hyperosmolar, it may be saline if the contrast is iso-osmolar, or it may be a contrast specific diluent which preserves specific desirable properties of the contrast during dilution, such as pH. It may be most convenient if contrast and diluent are available as a pair from the manufacturer. Diluent is so inexpensive that its waste is not a problem. It is essential that sterility be preserved and that all materials be compatible with the contrast material in use. Pharmaceutical companies are experienced and have developed considerable expertise in materials selection.

In the present disclosure, all embodiments employ an electronic control system which provides the proper fluid flows according to the instructions of the operator. The operator can either input information on the concentrations in the various containers, or the control system can read a bar code or other code on the bulk container which informs it of the volume and concentration in that bulk container. Also, there can be sensors which inform the control system when a bulk container empties, or the control system can keep track of the volume removed and anticipate when it will run out. Anticipation is preferred because an operator can then be informed during programming of the need to add fluid, rather than start a procedure and then run out.

There is a benefit to having back-up monitors for these important parameters. If the system anticipates when fluid runs out, there can still be fluid assurance sensors, in case a technician installs a partially used bottle. Especially when the contrast is being delivered to a patient, there needs to be a fluid assurance sensor to prevent the problem of air embolism. While concentration is not as critical, an improper concentration can necessitate repeat procedure. A sensor measuring electro-conductivity could be used for both concentration monitoring and fluid assurance. There are commercially available ultrasonic sensors designed to detect the presence or absence of fluid in a line. For example, U.S. Pat. No. 4,981,467 discloses such a detector.

Figure 1:
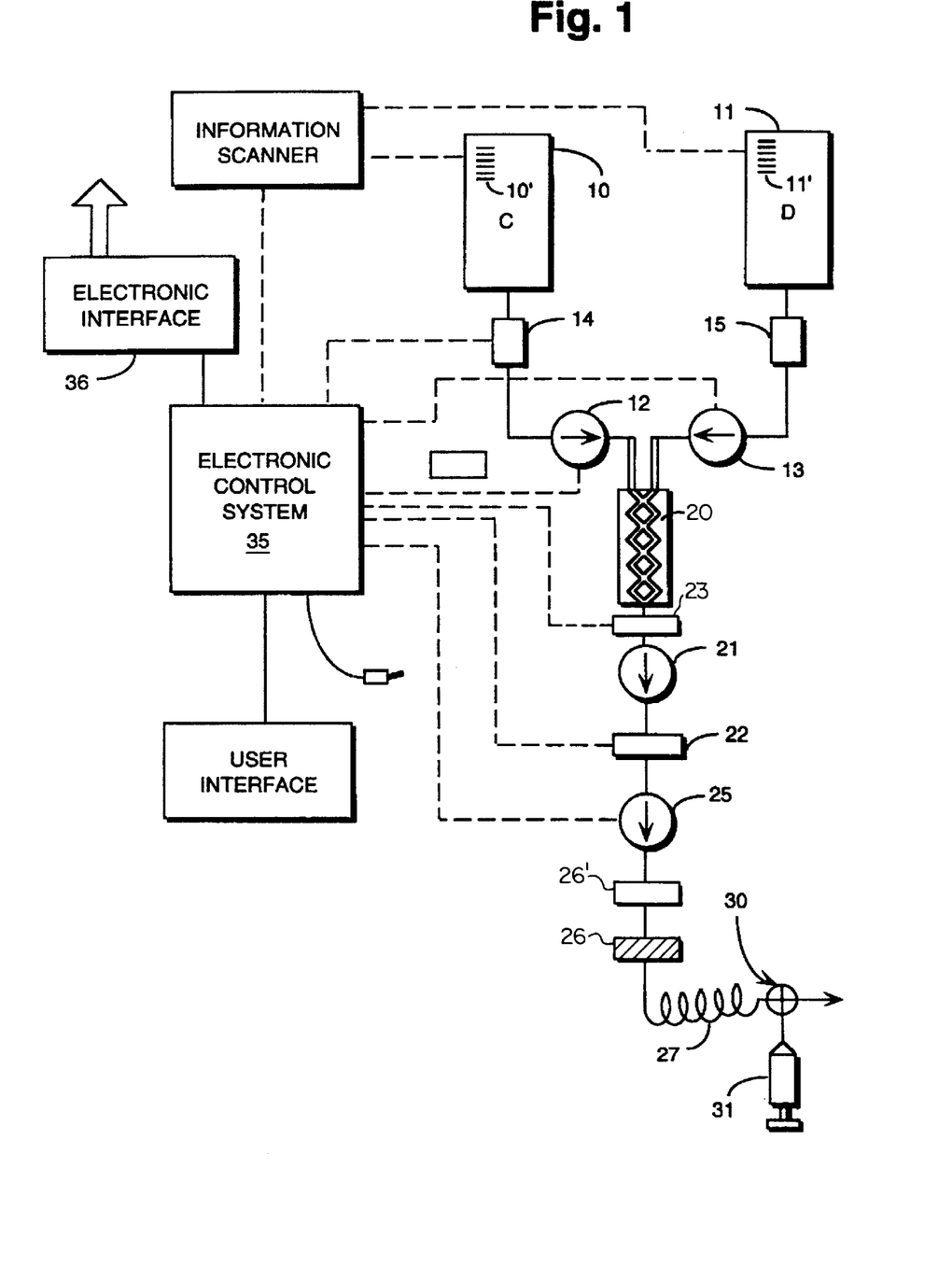
FIG. 1 diagrammatically shows an apparatus and a system for making constant changes in contrast solution strength and for injecting the fluid or the medium directly into the patient while minimizing the chance of patient-to-patient cross-contamination.

In the present instance, there are two classes of embodiments, the first being those that are directly connected to the patient and secondly, those which fill a dose container which is then moved to an injector for delivery to a patient. The first of these embodiments is shown in FIG. 1 where numeral 10 indicates a source of contrast medium which is in the form of a bulk container. Numeral 11 represents a similar container that is used to hold a supply of diluent, in the event that it is desired to reduce the concentration of the contrast medium contained within source 10. The containers may be rigid or flexible glass or a fluid compatible plastic such as polypropylene. If the containers are rigid, one of many known methods is used to vent the container with sterile air. A non-vented collapsible container is preferred to avoid air entry. A Metering pump 12 draws contrast from the contrast supply source 10 at the proper flow rate. The second metering pump 13 draws diluent (when desired) from the bulk reservoir 11 within which the supply of diluent is contained. A preferred metering pump is a precision peristaltic pump with santoprene tubing. A wall design similar to that of U.S. Pat. No. 5,230,614 would minimize the pulsatite flow characteristics. As the fluids are removed from the containers 10 and 11, they are heated by means of the heaters 14 and 15 so that they approximate body temperature. The heating, of course, decreases the viscosity of the contrast and makes the fluid more comfortable for the patient. (Rather than in line heaters, the bulk containers could be heated.)

Upon leaving the metering pumps 12 and 13, the fluids meet as they are joined and flow through a static mixer 20 that contains helical vanes. The company ConProTec makes many sizes and lengths, some with polypropylene vanes and a case. These static mixers are designed for mixing fluids with very different viscosities and varying dilution ratios. The exact length and diameter to be used will depend to some degree upon the viscosity of the contrast, dilution ranges, and flow rates. The flow is next through a concentration monitor 23. With metering pumps, this is optional but serves a useful verification function signaling if an incorrect mix occurs. Or, the metering pumps could be replaced by valves and the concentration monitor could continuously monitor and be part of the feed back control of the valves. The monitor measures a property which changes with concentration, such as electrical conducting, optical refraction index, rotation of polarized light, attenuation of sound, speed of sound, density, viscosity, or pressure drop through a fixed section. The mixture next flows through a back-flow prevention valve 21 which can be either a spring-loaded ball valve or a duck bill valve. This is an important feature of the overall device since it helps prevent cross-contamination when the device is used on another patient. By including valve 21 in the system, it is possible for fluid to flow only in one direction and there is no chance that contaminated fluid can be drawn back into the bulk fluid reservoirs from the patient's body.

Next, the fluid flows through a fluid assurance detector 22 which may be an ultrasonic detector so that the presence or absence of air in the fluid can be determined. Since these types of devices cannot detect small air bubbles, by being located before the pressurization pump 25, bubbles will be as large as possible. The fluid assurance detector helps minimize the chance that a broken line or human error can inject air into the patient.

Up until this point, the flow of the liquid has been at relatively low pressures. To inject the fluid through the connector tube 27 and catheter into the patient, relatively high pressures are needed: 300 psi for CT, up to 1200 psi for angiography, and 300 psi for MRI. Ultrasound contrast is presently not stable at high pressures, but its viscosity is similar to that of water so high pressures are not necessary. Presently this procedure is done by a powerful syringe pump, but these have the draw back that they can only inject one syringe full at a time. In the present embodiment, the pressurizing pump is a gear pump, with the housing and gears made from TPX. The parts could optionally be polycarbonate or Teflon coated polycarbonate. This gives the clarity needed to check for bubbles, and the drug compatibility of Teflon. The shaft of the gear pump is connected to an electric motor with a spline or other coupling mechanism so that the pump head can be removed and disposed of when required. Depending upon the fluid path which leads to the gear pump and the turbulence within the pump, enough mixing could take place that the static vane mixer could be eliminated. Fassbender in U.S. Pat. No. 3,349,713 teaches how a gear pump can be modified to accomplish the mixing of fluids of different viscosities. Because of the widely varying flow rate, this is not possible for all applications, but some would benefit by the elimination of the mixing element and the incorporation of its function into the pump.

The pressurized fluid flows through a 0.2 micron "sterilizing" filter 26. These filters are becoming a standard way to assure sterility of the solution. Its purpose here is to prevent migration of any bacteria from the patient into the pump. In cooperation with the backflow valve, cross-contamination in minimized. The sterile filter prevents bacteria from swimming up stream and the back flow preventer stops passive pathogens from being carried backward through the sterile filter. The fluid coming out of the pump is sterile. The area of the sterile filter will need to be adjusted to accommodate the flow rates of the various procedures while maintaining a reasonable pressure drop. A flexible connector tube 27, which is preferably sterile, carries the fluid to the patient. These are commercially available, usually made out of PVC. This component is disposed of after each patient so that it does not need to have long term compatibility with contrast medium.

At the patient, there is a three-way stopcock 30 and a hand syringe 31. This part can be used for several things. It can be used to aspirate blood and thus, verify good IV catheter placement in CT. It can be used to inject other medications. It can also be used to fill a hand syringe which can be removed and used for test injections during angiography. With one position of the stopcock, the fluid flows straight into the patient.

The present apparatus includes an electronic control system (ECS) 35 to assure that the needs of the patient are met safely. ECS 35 gets information on the contents of the bulk reservoirs 10 and 11. The preferred method is to read bar codes indicated by numerals 10' and 11' respectively. Another way is to quiz the operator to enter the data each time a bulk reservoir is changed, and then store that information. The operator would read the label on or packaged with the bulk reservoir, and enter the appropriate data. This need only be done when a bulk reservoir is changed.

With each injection, the operator needs to tell the system what to do. The data most similar to present practice is: 1) the concentration desired, 2) the flow rate, and 3) the total volume to be delivered. Present practice also includes multiple phases with various constant flow rates during each phase. This system would allow various contrast concentrations during each phase as well.

However, given the capabilities of this system, a preferred set of information is: 1) the procedure being done, and 2) the patient weight. This way the contrast dose could be optimized for the patient. The algorithm would have been previously provided information on milligrams of iodine per kilogram of patient for each procedure when the system was first installed in the hospital. It could display concentration, flow rate and volume for operator verification, if the operator desired. An electronic interface 36 is shown which can connect to the hospital information system to get information on the patient, such as weight. Then the operator would only have to input the patient number. The electronic interface could also be connected to the imaging equipment. It could send or receive information so that, for instance, the operator only needs to program the CT scanner with number of slices and body section, and this would be transmitted to the contrast delivery system to be used in determining flow rates and delays. The electronic interface would also be used to let the scanner trigger the contrast delivery system or vice versa, after the appropriate delays. A hard copy printer may be optionally part of the user interface, receiving data from the ECS. This can print a record of the actual injection for insertion into the patient records. The output may be alphanumeric or be a graphical representation of the injection.

The operation of delivering fluid to the patient can be started by the operator with a start switch on the contrast delivery system, or from the console of the scanner. There would need to be an arming procedure similar to that of present injectors to help assure patient safety.

In CT, usually only one injection is given, sometimes with pauses and changes in flow rates. As the end of the injection is reached, contrast can be conserved if the contrast flow is stopped and the diluent flow continued so the "bolus" of diluted contrast is flushed out of the tubing and into the patient. In angiography, several injections may be used. It is necessary to flush only after the last injection, although no harm, except injecting a little extra fluid, occurs if the flush follows each injection.

Another form of waste is using contrast to prime the fluid path which is disposed of with each patient, especially if the concentration has not yet been decided upon. The flush or diluent fluid is much cheaper than the contrast and of lower viscosity, so it can be used to prime the line and make sure that all air has been removed from the path to the patient.

The present invention envisions that the "per patient" disposable portion of the apparatus starts just above the sterile filter 26 and ends at the patient. This "per patient" connection 26' may be made farther upstream, with the result that more of the fluid path is disposed of. This connection must be broken after one patient and made before the next. After the connection to one patient is removed, the connection for the next patient is quickly installed and sterilized, as by means of ultraviolet illumination. The present practice of making aseptic connections as discussed in U.S. Pat. No. 5,207,642 involves inserting a spike through a resilient member. This is common practice and is acceptable when used on one patient although it does not provide the level of sterility provided by ultraviolet illumination. The remainder of the connector tube and the patient connection end can remain in the sterile bag, ready for the patient who may come in the next hour or in the next few days. To further enhance sterility, the remainder of the fluid path connecting containers 10, 11; heaters 14, 15; metering pumps 12 and 13, etc., is disposable, in which case the "per patient" connection 26' would be moved farther upstream, as described above, to the desired position, bearing in mind that the disposable portion is defined as everything below the connection 26', inclusive of elements downstream of the connection 26'. For example, if the connection 26' is positioned along the fluid path that connects the containers, heaters or metering pumps, everything downstream of the connection 26', e.g., pump 25, detector 22 and/or valve 21, would be included with the disposable portion. However, it is only recommended that the disposable portion be replaced when the bulk contrast container be replaced. Thus, this system needs no active sterilization mechanism nor any toxic sterilants.

It is possible for the bulk fluid containers to feed more than one imaging suite, and thus, more than one patient at the same time. With large enough containers, this would be desireable. Each imaging suite would have all the components shown in FIGS. 1 or 2, except that they would share containers 10 and 11 from which fluid could be drawn simultaneously. Or, there could be just one central ECS, with a user interface in each imaging suite.

It is possible to operate the device without the addition of any diluent. In this case, the static mixer could be removed since there will be no change in the concentration of the contrast medium. This system provides several simplifications but does require a departure from the normal practice that has existed in hospital practices until this time. In operating by this method, the operator would put in patient weight and the procedure, the electronic control system would calculate total volume and flow rate and the patient weight and procedure would determine the milligrams of Iodine per second that were needed. The contrast delivery system would then deliver at the flow rate needed to provide the proper mgI/s. with the removal of the limitations of syringe and bottle size, concentration is a redundant parameter when flow rate can be freely determined.

Figure 2:
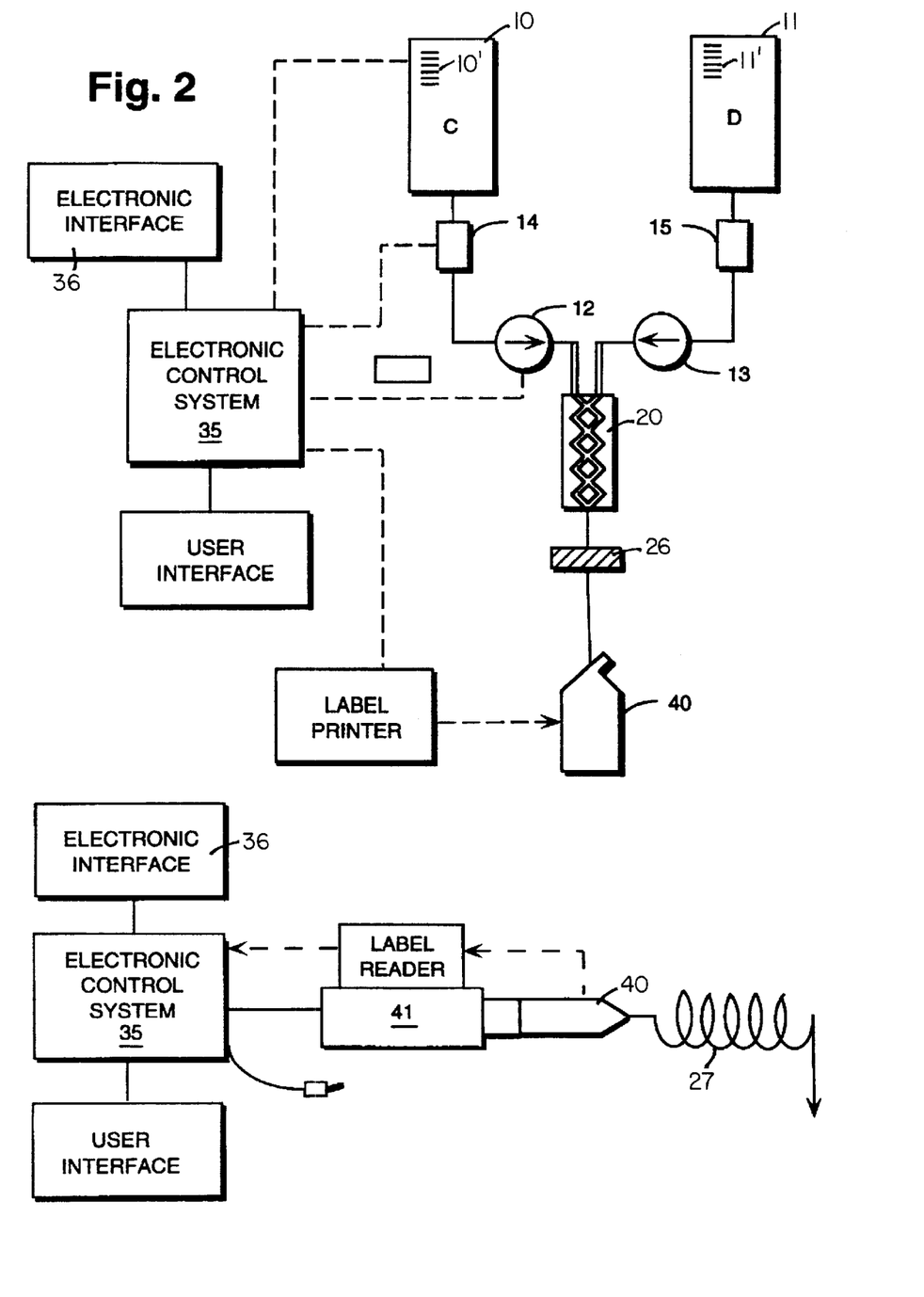
FIG. 2 is an illustration similar to FIG. 1 showing one method for filing dose containers and subsequently, putting the dose containers in an injector head for use with a patient.

In the apparatus shown in FIG. 2, the fluid flows from the static mixer to a dose container 40. When filled with the proper amount of the desired concentration, the dose container is separated from the filling section and installed in the injecting section 41. This embodiment has two benefits. Cross-contamination is more positively prevented because air intervenes between the patient and the bulk reservoirs. The sterile filter may still be used but ideally it and the back flow valve are less significant or optional. Secondly, the system can utilize existing contrast injectors which hospitals already own, thus, reducing capital costs. It is not the preferred embodiment because it imposes limitations based upon syringe size.

The dose container need not be physically moved from one machine to another. It may stay in place, but the connection to the static mixer is opened and the connection to the patient is made. Interlocks would assure that a syringe could not be refilled after being connected to a patient. This prevents contamination by pathogens from the patient.

FIG. 2 shows the filling station and the injector with separate electronic control systems. To transfer information, a label 42 is printed and attached to the dose container. This label is read by the contrast injector and used to set the program. In the event that the label is not machine readable then the label can be printed in human readable text and the operator could program the contrast injector.

The embodiment presented above is the one preferred by the inventors, but it is possible for someone skilled in the art to rearrange the order of the components in the fluid path and still accomplish the goals of this device. In particular, the first component could be pressurizing pumps which create high enough pressures to drive the fluid through the remainder of the system and into the patient. Or, the bulk containers could be pressurized, and the metering pumps could then be metering valves. Mixing could be after the sterile filters, right before injection into the patient. These are only a few of the reasonable permutations. It is also a reasonable extension of this idea that more than two bulk containers may be used. These can sequentially or simultaneously dispense their fluid as medically necessary. They may contain various medicines to be diluted or not. An example is heparinized saline to prevent clotting in the catheter.

Although the present invention has been described in terms of preferred embodiments, the present description is given by way of example and is not intended to be limiting to the scope of the invention described and claimed.

What is claimed is:

1. A disposable unit for delivering fluid medium from a supply source to a plurality of patients, the disposable unit comprising:

a sterile patient supply tube for a patient of said plurality of patients;

means for receiving pressurized fluid medium into the patient supply tube; and contamination prevention means configured and arranged to be positioned between the supply source and the patient, for precluding backflow of material from the patient to the fluid medium receiving means, for preventing contamination of the fluid medium receiving means, and for preventing cross-contamination between said plurality of patients.

2. A disposable unit according to claim 1, wherein the contamination prevention means comprises unidirectional flow means for allowing passage of fluid medium from the fluid medium receiving means to the patient but not in a reverse direction.

3. A disposable unit according to claim 2, wherein the unidirectional flow means comprises a valve.

4. A disposable unit according to claim 2, wherein the contamination prevention means comprises a sterilizing filter.

5. A disposable unit according to claim 4, wherein the contamination prevention means further comprises a backflow prevention valve.

6. A disposable unit according to claim 1, wherein the patient supply tube comprises a flexible connector tube for transporting the fluid to the patient.

7. A disposable unit according to claim 6, wherein the flexible connector tube is connected to a stopcock for allowing fluid to flow to the patient.

8. A disposable unit according to claim 1, comprising a first disposable patient supply tube for connecting to a first patient and a second disposable patient supply tube for connecting to a second patient.

9. A disposable unit for delivering fluid medium to a patient, comprising:

a sterile patient supply tube for receiving the fluid medium; and a contamination prevention unit connected to the sterile patient supply tube, wherein the contamination prevention unit precludes backflow of material from the patient upstream of the sterile patient supply tube, prevents contamination of the fluid medium upstream of the sterile patient supply tube, and prevents cross-contamination between patients, and wherein the disposable unit further comprises a first disposable fluid path for connecting to a first patient and a second disposable fluid path for connecting to a second patient.

10. A unit for delivering a pressurized fluid medium from a supply source to a plurality of patients, the unit comprising:

a sterile patient supply tube for a patient of said plurality of patients;

a connector that connects the patient supply tube to the pressurized fluid medium;

a filter configured and arranged to be positioned between the connector and the patient, the filter preventing contamination of the connector; and a valve, in communication with the filter, that precludes backflow of material from the patient to the connector, the valve, in conjunction with the filter, preventing cross-contamination between said plurality of patients.

11. A disposable unit for delivering pressurized fluid medium from a supply source for providing said pressurized fluid to a plurality of patients, comprising:

a patient supply tube for a patient of said plurality of patients;

a connector that connects the patient supply tube to the pressurized fluid medium; and a contamination prevention unit structured and configured to be located between the connector and the patient, the contamination prevention unit 1) preventing contamination of the connector, 2) precluding upstream flow of at least one of the pressurized fluid medium and bacteria from the patient to the connector, and 3) preventing cross-contamination between said plurality of patients.

12. A disposable unit according to claim 11, wherein the contamination prevention unit comprises a one-way valve.

13. A disposable unit according to claim 12, wherein the contamination prevention unit further comprises a filter.

14. A disposable unit according to claim 11, wherein the contamination prevention unit comprises a filter.

15. A fluid path apparatus for delivering fluid medium along a fluid path, the fluid path apparatus comprising:

a reusable portion of the fluid path, the reusable portion including at least a supply source that provides the fluid medium to a plurality of patients;

a disposable portion of the fluid path, the disposable portion being connectable to the reusable portion, and including at least a sterile patient supply tube for a patient of said plurality of patients, the patient being adapted to be connected to the reusable portion via the disposable portion of the fluid path; and a contamination prevention unit positioned along the fluid path and configured and arranged to be positioned between the supply source and the patient, the contamination prevention unit preventing cross-contamination between said plurality of patients.

16. An apparatus according to claim 15, wherein the contamination prevention unit comprises a portion of the disposable portion.

17. An apparatus according to claim 15, wherein the contamination prevention unit comprises a portion of the reusable portion.

18. An apparatus according to claim 15, wherein the contamination prevention unit comprises a sterile filter.

19. An apparatus according to claim 18, wherein the sterile filter comprises a portion of the disposable portion.

20. An apparatus according to claim 15, wherein the contamination prevention unit comprises a one-way valve.

21. An apparatus according to claim 20, wherein the one-way valve comprises a portion of the disposable portion.

22. An apparatus according to claim 20, wherein the one-way valve comprises a portion of the reusable portion.

23. A fluid apparatus for delivering fluid medium along a fluid path, the fluid path apparatus comprising:

a reusable portion of the fluid path including at least a supply source that provides the fluid medium to a plurality of patients;

a disposable portion of the fluid path, the disposable portion being connectable to the reusable portion, and including at least a sterile patient supply tube for a patient of said plurality of patients, the patient being adapted to be connected to the reusable portion via the disposable portion of the fluid path; and a backflow prevention unit positioned along the fluid path and configured and arranged to be positioned between the supply source and the patient, the backflow prevention unit precluding backflow of material from the patient to the reusable portion to thereby prevent contamination of the reusable portion.

24. An apparatus according to claim 23, wherein the backflow prevention unit comprises a portion of the disposable portion.

25. An apparatus according to claim 23, wherein the backflow prevention unit comprises a portion of the reusable portion.

26. An apparatus according to claim 23, wherein the backflow prevention unit comprises a sterile filter.

27. An apparatus according to claim 26, wherein the sterile filter comprises a portion of the disposable portion.

28. An apparatus according to claim 23, wherein the backflow prevention unit comprises a one-way valve.

29. An apparatus according to claim 28, wherein the one-way valve comprises a portion of the disposable portion.

30. An apparatus according to claim 28, wherein the one-way valve comprises a portion of the reusable portion.

31. A fluid path apparatus for delivering fluid medium along a fluid path, the fluid path apparatus comprising:

a reusable portion of the fluid path including at least a supply source that provides the fluid medium to a plurality of patients;

a disposable portion of the fluid path, the disposable portion being connectable to the reusable portion, and including at least a sterile patient supply tube for a patient of said plurality of patients, the patient being adapted to be connected to the reusable portion via the disposable portion of the fluid path;

a backflow prevention unit positioned along the fluid path and configured and arranged to be positioned between the supply source and the patient, the backflow prevention unit precluding backflow of material from the patient to the reusable portion to thereby prevent contamination of the reusable portion; and a contamination prevention unit positioned along the fluid path and configured and arranged to be positioned between the supply source and the patient, the contamination prevention unit preventing cross-contamination between said plurality of patients.

32. An apparatus according to claim 31, wherein the contamination prevention unit comprises a portion of the disposable portion.

33. An apparatus according to claim 31, wherein the contamination prevention unit comprises a portion of the reusable portion.

34. An apparatus according to claim 31, wherein the contamination prevention unit comprises a sterile filter.

35. An apparatus according to claim 34, wherein the sterile filter comprises a portion of the disposable portion.

36. An apparatus according to claim 31, wherein the contamination prevention unit comprises a one-way valve.

37. An apparatus according to claim 36, wherein the one-way valve comprises a portion of the disposable portion.

38. An apparatus according to claim 36, wherein the one-way valve comprises a portion of the reusable portion.

39. An apparatus according to claim 31, wherein the backflow prevention unit comprises a portion of the disposable portion.

40. An apparatus according to claim 31, wherein the backflow prevention unit comprises a portion of the reusable portion.

41. An apparatus according to claim 31, wherein the backflow prevention unit comprises a sterile filter.

42. An apparatus according to claim 41, wherein the sterile filter comprises a portion of the disposable portion.

43. An apparatus according to claim 31, wherein the backflow prevention unit comprises a one-way valve.

44. An apparatus according to claim 43, wherein the one-way valve comprises a portion of the disposable portion.

45. An apparatus according to claim 43, wherein the one-way valve comprises a portion of the reusable portion.

46. An apparatus according to claim 31, wherein the contamination prevention unit and the backflow prevention unit comprise a portion of the disposable portion.

47. An apparatus according to claim 31, wherein the contamination prevention unit and the backflow prevention unit comprise a portion of the reusable portion.

48. An apparatus according to claim 31, wherein at least one of the contamination prevention unit and the backflow prevention unit comprises a sterile filter.

49. An apparatus according to claim 48, wherein the sterile filter comprises a portion of the disposable portion.

50. An apparatus according to claim 31, wherein at least one of the contamination prevention unit and the backflow prevention unit comprises a one-way valve.

51. An apparatus according to claim 50, wherein the one-way valve comprises a portion of the disposable portion.

52. An apparatus according to claim 50, wherein the one-way valve comprises a portion of the reusable portion.

53. An apparatus according to claim 31, wherein at least one of the backflow prevention unit and the contamination prevention unit comprises a portion of the disposable portion, and another of the contamination prevention unit and the backflow prevention unit comprises a portion of the reusable portion.

* * * * *

UNITED STATES PATENT AND TRADEMARK OFFICE
CERTIFICATE OF CORRECTION

| | | |
|---|---|---|
| PATENT NO. | : 6,442,418 B1 | Page 1 of 1 |
| DATED | : August 27, 2002 | |
| INVENTOR(S) | : Russell Morrison Evans, III and Arthur E. Uber, III | |

It is certified that error appears in the above-identified patent and that said Letters Patent is hereby corrected as shown below:

<u>Title page,</u>
Item [62], should read:
-- Related U.S. Application Data
[62] Continuation of application No. 08/919,742, filed on Aug. 28, 1997, now Pat. No. 5,885,216, which is a division of application No. 08/534,081, filed on Sep. 22, 1995, now Pat. No. 5,806,519, which is a continuation of application No. 08/144,462, filed on Oct. 28, 1993, now abandoned. --

<u>Column 1,</u>
Lines 4 through 9, should read:
-- This is a continuation of application Ser. No. 08/919,742, filed on Aug. 28, 1997, now U.S. Pat. No. 5,885,216, which is a division of application Ser. No. 08/534,081, filed on Sep. 22, 1995, now U.S. Pat No. 5,806,519, which is a continuation of application Ser. No. 08/144,462, filed on Oct. 28, 1993, now abandoned. --

Signed and Sealed this

Third Day of June, 2003

JAMES E. ROGAN
*Director of the United States Patent and Trademark Office*